US009349535B2

(12) United States Patent
Hagedorn et al.

(10) Patent No.: US 9,349,535 B2
(45) Date of Patent: May 24, 2016

(54) METHOD AND APPARATUS FOR MANUFACTURING ISOTROPIC MAGNETIC NANOCOLLOIDS BY PULSED LASER ABLATION

(71) Applicant: Metastable Materials, Inc., Ann Arbor, MI (US)

(72) Inventors: Kevin Hagedorn, Ann Arbor, MI (US); Henrietta Malizia, Myrtle Beach, SC (US)

(73) Assignee: Metastable Materials, Inc., Ann Arbor, MI (US)

( * ) Notice: Subject to any disclaimer, the term of this patent is extended or adjusted under 35 U.S.C. 154(b) by 0 days.

(21) Appl. No.: 14/573,807

(22) Filed: Dec. 17, 2014

(65) Prior Publication Data
US 2015/0170807 A1 Jun. 18, 2015

Related U.S. Application Data

(60) Provisional application No. 61/916,889, filed on Dec. 17, 2013.

(51) Int. Cl.
| | |
|---|---|
| *H01F 1/153* | (2006.01) |
| *H01F 1/147* | (2006.01) |
| *H01F 41/20* | (2006.01) |
| *B82Y 15/00* | (2011.01) |
| *G01N 33/543* | (2006.01) |
| *C22C 45/00* | (2006.01) |
| *C22C 45/02* | (2006.01) |
| *C22C 45/04* | (2006.01) |

(52) U.S. Cl.
CPC .............. *H01F 41/205* (2013.01); *B82Y 15/00* (2013.01); *C22C 45/008* (2013.01); *C22C 45/02* (2013.01); *C22C 45/04* (2013.01); *G01N 33/54326* (2013.01); *G01N 2446/00* (2013.01); *G01N 2446/86* (2013.01); *Y10T 428/2982* (2015.01)

(58) Field of Classification Search
CPC ...... C22C 45/008; C22C 45/02; C22C 45/04; B82Y 15/00; G01N 33/5435; G01N 33/54326; G01N 2446/86; G01N 2446/00; H01F 1/442
See application file for complete search history.

(56) References Cited

U.S. PATENT DOCUMENTS

| | | | |
|---|---|---|---|
| 3,965,463 | A | 6/1976 | Chaudhari et al. |
| 4,523,621 | A | 6/1985 | Ray |
| 4,743,311 | A | 5/1988 | Schultz et al. |
| 4,913,745 | A | 4/1990 | Sato |
| 5,288,339 | A | 2/1994 | Schnitzke et al. |
| 5,356,713 | A | 10/1994 | Charmot et al. |
| 5,585,020 | A | 12/1996 | Becker et al. |
| 5,766,764 | A | 6/1998 | Olli et al. |
| 6,312,768 | B1 | 11/2001 | Rode et al. |
| 6,478,889 | B2 | 11/2002 | Kanekiyo |
| 6,514,481 | B1 | 2/2003 | Prasad et al. |
| 8,287,664 | B2 | 10/2012 | Brunner |
| 8,298,352 | B2 | 10/2012 | Brunner |
| 8,372,218 | B2 | 2/2013 | Nuetzel et al. |
| 8,802,234 | B2 | 8/2014 | Che et al. |
| 2005/0034787 | A1 | 2/2005 | Song et al. |
| 2008/0187684 | A1 | 8/2008 | Hu et al. |
| 2010/0196192 | A1 | 8/2010 | Liu et al. |
| 2012/0012778 | A1 | 1/2012 | Tilley et al. |
| 2012/0318412 | A1 | 12/2012 | Ohta et al. |
| 2013/0034492 | A1 | 2/2013 | Hansen et al. |
| 2013/0150231 | A1 | 6/2013 | Hagedorn et al. |
| 2013/0243699 | A1 | 9/2013 | Wang et al. |
| 2013/0309702 | A1 | 11/2013 | Kim et al. |

FOREIGN PATENT DOCUMENTS

| | | |
|---|---|---|
| RU | 2 364 472 C2 | 8/2009 |
| RU | 2 458 705 C1 | 8/2012 |
| RU | 2 465 008 C1 | 10/2012 |
| WO | 2005/052960 A2 | 6/2005 |

OTHER PUBLICATIONS

K. Affolter, et al., "Laser Produced Amorphous Phases in Nb—Si and V—Si Thin Films," Journal of Non-Crystalline Solids 55, pp. 387-393 (Noth-Holland Publishing Co. 1983).
K. J. Carroll, et al., "Annealing of amorphous FexCo100-x nanoparticles synthesized by a modified aqueous reduction using NaBH4," Journal of Applied Physics 107, 09A303 (Am. Institute of Physics 2010).
K. J. Carroll, et al., "Nonclassical crystallization of amorphous iron nanoparticles by radio frequency methods," Journal of Applied Physics 107, 09A302 (Am. Institute of Physics 2010).
F. Delogu, "Atomistic mechanism of the formation of a nanometer-sized amorphous metal by Kirkendall effect," Materials Chemistry and Physics 125, pp. 390-396 (Elsevier B.V. 2010).
M. V. Gorokhov, et al., "Formation of Structures from Amorphous Metallic Nanoparticles by Dispersing Metal Drops Continuously Charging in an Electron Beam," Technical Physics, vol. 57, No. 6, pp. 868-873 (Pleiades Publishing, Ltd. 2012).
M. Gorokhov, et al., "New technique of amorphous metal nanoparticles production by liquid drop breakup in an electron beam," Physica Status Solidi A 209, No. 6, pp. 1036-1041 (Wiley-VCH 2012).
R. Hasegawa, et al., "Magnetic inductor based on nanosize amorphous metal powder," Journal of Non-Crystalline Solids 353, pp. 773-776 (Elsevier B.V. 2007).

(Continued)

*Primary Examiner* — Carol M Koslow
(74) *Attorney, Agent, or Firm* — Young Basile Hanlon & MacFarlane, P.C.

(57) ABSTRACT

Disclosed herein are systems, methods, and apparatuses for manufacturing highly isotropic magnetic nanoparticles. In particular, manufacturing of spherical and amorphous particles suspended in a solvent by irradiating alloy targets submerged in a solvent using nanosecond-scale laser pulses is disclosed. The absence of shape and crystalline anisotropy in the particles yields a colloidal suspension with excellent soft magnetic properties which can be used to improve the performance of various medical diagnostic devices and consumer electronics.

11 Claims, 7 Drawing Sheets

(56) References Cited

OTHER PUBLICATIONS

C. F. Vardeman II and J. Daniel Gezelter, "Simulations of Laser-Induced Glass Formation in Ag—Cu Nanoparticles," J. Phys. Chem. C, vol. 112, No. 9, pp. 3283-3293 (American Chemical Society 2008).

G. Kataby, et al., "Blocking temperatures of amorphous iron nanoparticles coated by various surfactants," Applied Surface Science, 201, pp. 191-195 (Elsevier Science B.V. 2002).

M. E. McHenry, et al., "Amorphous and nanocrystalline materials for applications as soft magnets," Progress in Materials Science 44, pp. 291-433 (Elsevier Science Ltd. 1999).

K. V. P. M. Shafi, et al., "Sonochemical Preparation of Nanosized Amorphous NiFe2O4 Particles," Journal of Physical Chemistry B 1997, pp. 6409-6414 (American Chemical Society 1997).

Y. Song, et al., "Stable Amorphous Cobalt Nanoparticles Formed by an in Situ Rapidly Cooling Microfluidic Process," Langmuir: The ACS Journal of Surfaces and Colloids, 25(17), pp. 10209-10217 (Am. Chem. Soc. 2009).

T. Toshima, et al., "Magnetic properties of CoZr Amorphous Films Prepared by Low Energy Ion Beam Sputtering," IEEE Transactions on Magnetics, vol. 22, No. 5, pp. 1110-1112 (IEEE Sep. 1986).

S. Vitta, et al., "Metastable Phases Formed by Nanosecond Laser-quenching of Metals and Binary Alloys," Materials Science and Engineering, 98, pp. 105-109 (Elsevier Sequoia 1988).

S. Vitta, et al., "Rapid solidification of cobalt—titanium alloys induced by nanosecond laser pulses," Materials Science and Engineering, A179/A180, pp. 243-248 (Elsevier Sequoia 1994).

M. Von Allmen, "Metastable phases in laser-irradiated Pt—Si and Pd—Si thin films," Applied Physics Letters, vol. 37, No. 1, pp. 84-86 (AIP Publishing 1980).

T. Yano, et al., "Amorphous alloy films deposited by excimer laser ablation using sintered Ta—Ni targets," Journal of Materials Science Letters 15, pp. 1994-1996 (Chapman & Hall 1996).

METHOD AND APPARATUS FOR MANUFACTURING ISOTROPIC MAGNETIC NANOCOLLOIDS BY PULSED LASER ABLATION

CROSS-REFERENCE TO RELATED APPLICATION

This application claims the benefit under 35 U.S.C. §119(e) of U.S. provisional application No. 61/916,889, filed Dec. 17, 2013, which is incorporated herein in its entirety by reference.

TECHNICAL FIELD

This disclosure relates to manufacturing magnetic nanocolloids and magnetic nanocomposite nanocolloids using pulsed laser ablation.

BACKGROUND

Magnetic assays can be used to identify, locate or quantify biological materials by binding a magnetic particle to a biologic analyte and using a magnetic sensor to detect the magnetic particle and thereby quantify the biologic analyte. This can be an effective manner with which to detect biologic analyte since biological materials generally do not exhibit natural magnetism, therefore any magnetic signal sensed can be assumed to originate from the magnetic nanoparticle tag.

Amorphous metals can have many desirable properties for a variety of industrial applications. An "amorphous metal" is a metal which has a disordered atomic structure. Related materials include "magnetic nanocomposites" which consist of metal crystals grown in an amorphous metal matrix. The metal crystals typically having a size of 1 to 5 nm.

Amorphous metals and magnetic nanocomposites can be used in electronic devices. For example, amorphous metals can be used in high efficiency power transformers. Magnetic nanocomposites can be used in power transformers which operate at temperatures above 400° C. Amorphous metals can also be used in anti-theft tags, for example.

SUMMARY

Aspects of disclosed implementations include magnetic particles with the composition $X_{1-a}Y_a$, where X is one of the elements Co or Fe or a combination thereof, Y is a transition metal which forms a eutectic with Co or Fe, such as Zr, Ti, Sc, Ta, Hf, Y, La, Si, B or Nd or a combination thereof and wherein the value of a is between 0.4 and 0.02. The particles can have an average size between 15 and 45 nm and can be spherical or nearly spherical, with an aspect ratio less than 5:1, or more particularly having an aspect ratio of less than 1.3:1. The atomic structure of these particles can be amorphous. These particles can exist as a colloidal suspension in liquid or as a dry powder. The particles can be coated with an inert material such as Au, $SiO_2$ or carbon. In addition, organic molecules, for example proteins or nucleic acid, can be attached to the surface of the particles or to the surface of the inert material that coats the particles to create a targeted magnetic particle.

Another aspect of disclosed implementations include magnetic nanocomposites particles with the composition $X_{1-a-b}Y_aZ_b$, where X is one of the elements Co, Fe, Ni or a combination thereof; wherein Y is a transition metal such as Zr, Ti, Sc, Ta, Hf, Y, La or Nd, which can form a eutectic with Co or Fe, or a glass former such as Si or B, or a combination of these elements; where Z is one of the group of elements Au, Ag and Cu; wherein the value of a is between 0.4 and 0.02 and the value of b is between 0.05 and 0.001. The particles can have an average size between 15 and 45 nm and are spherical or nearly spherical with an aspect ratio less than 2:1, or more particularly having an aspect ratio of less than 1.3:1. These particles can exist as a colloidal suspension in liquid or as a dry powder. The atomic structure can be a mixture of crystalline and amorphous volumes distributed through the particle. The particles can be coated with an inert material such as Au, $SiO_2$ or carbon. Furthermore, organic molecules, for example proteins, can be attached to the surface of the particles or to the surface of the inert material that coats the particles.

Aspects of disclosed implementations include systems, methods, and apparatuses for manufacturing a colloidal suspension of isotropic magnetic particles including irradiating, with a pulsed laser, a target in a solvent wherein the pulsed laser can produce laser pulses having a pulse duration between 1 ps and 1 μs at a wavelength between 200 nm and 1500 nm at a pulse repetition rate of at least 10 Hz and a fluence greater than 2 J/cm². The laser beam can be scanned across the surface of the target, where the target can include a metallic composite with the composition $X_{1-a}Y_a$, where X is one of the group of elements Co, Fe, Ni, or a combination thereof, Y is an element from the group of Zr, Ti, Sc, Ta, Hf, Y, La, Nd or a combination thereof and a has a value between 0.4 and 0.02. The solvent can be an organic solvent and photothermal fragmentation can be used to modify the size or shape of the particles included in the colloidal suspension. Centrifugation can be used to further modify the size of the particles included in the colloidal suspension. The surface of the particles or the composition of the solvent can be changed to suit the application after the desired size distribution has been obtained, which can include modifying the surface of the particles with Au, $SiO_2$ or carbon or can include replacing part or the entirety of the solvent with a polymer or another solvent. The technique can further include attaching organic molecules including proteins to the surface of the particles or to the surface of the Au, $SiO_2$ or carbon which can coat the particles.

Other aspects of disclosed implementations include systems, methods, and apparatuses for manufacturing a colloidal suspension of nanocomposite particles including irradiating, with a pulsed laser, a target in a solvent wherein the pulsed laser produces laser pulses having a pulse duration between 1 ps and 1 μs at a wavelength between 200 nm and 1500 nm and a fluence of at least 2 J/cm² with a repetition rate greater than 10 Hz. The beam can be scanned across the surface of the target and the target can include a metallic composite with the composition $X_{1-a-b}Y_aZ_b$, where X can be the magnetic elements Co, Fe or Ni or a mixture thereof, Y is a transition metal or glass former which forms a eutectic with the elements of X, such as the transition metals Zr, Ti, Sc, Ta, Hf, Y, La, Nd or the glass formers Si or B or a combination thereof; where Z is one of the group of elements Au, Ag and Cu; where a has a value between 0.4 and 0.02 and b has a value between 0.05 and 0.001. The solvent can be an organic solvent and photothermal fragmentation can be used to modify the size or shape of the particles which comprise the colloidal suspension. Centrifugation can be used to further modify the size of the particles included in the colloidal suspension. After the desired size distribution is obtained, the particles can be sealed in a high pressure vial and heated to between 100 and 800° C. for at least 2 min to induce nucleation of metal crystallites in the particle. The surface of the particles or the composition of the solvent can be changed to suit the application, which can include modifying the surface of the particles with Au, $SiO_2$, C or a polymer, or can include replacing part or the entirety of the solvent with a polymer or another solvent. The method can further include attaching organic molecules including proteins to the surface of the particles or to the surface of the Au, $SiO_2$, C or polymer which coats the particles.

BRIEF DESCRIPTION OF THE DRAWINGS

The various features, advantages and other uses of the present apparatus will become more apparent by referring to the following detailed description and drawing in which.

DETAILED DESCRIPTION

Figure 1:
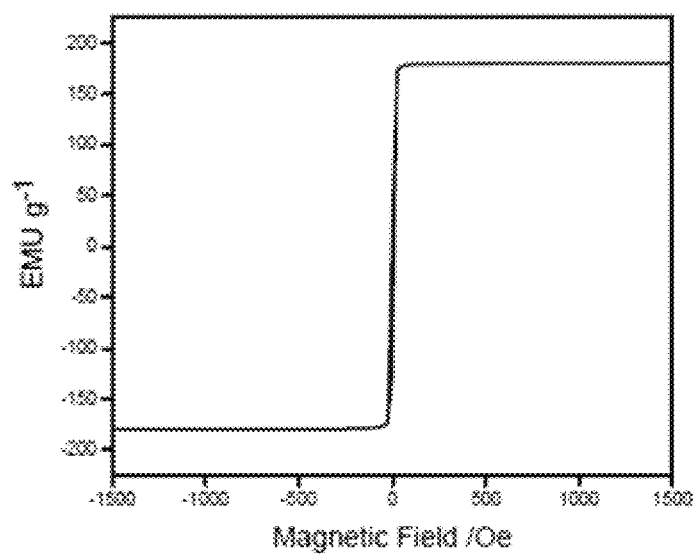
FIG. 1 is the calculated DC hysteresis curve for 20 nm isotropic $Co_{92}Zr_8$ particles in accordance with one disclosed implementation.
Figure 2:
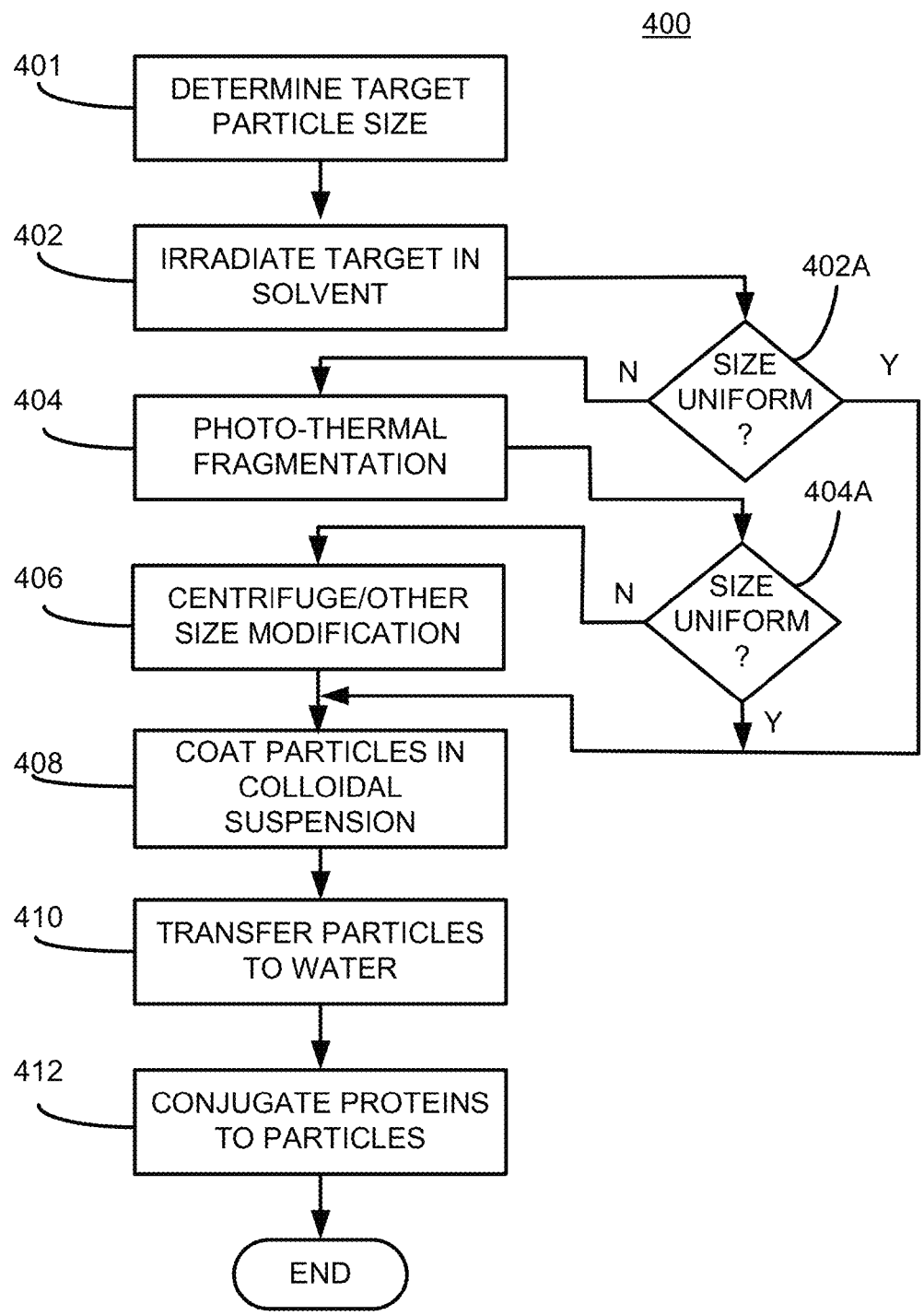
FIG. 2 is a flowchart diagram of a process for manufacturing a colloidal suspension of isotropic magnetic particles in accordance with one disclosed implementation.

The following terms are defined as follows herein:

"Nanoparticles" refers to objects having a size in the range of 1 nm to 1000 nm in at least one dimension.

"Colloidal suspension" refers to particles suspended in a liquid by Brownian motion. Therefore, a colloidal suspension of gold particles refers to gold particles suspended in a liquid by Brownian motion.

"Amorphous" refers to particles with no regular ordering over distances greater than 1 nm. For the purposes of this document, a material can be considered amorphous if it has no identifiable lattice fringes when examined with high resolution electron microscopy or the material exhibits a select area electron diffraction pattern which consists of a single diffuse ring with a roughly Gaussian intensity distribution.

"Magnetic Nanocomposite" refers to a material that is a mixture of amorphous and crystalline regions. These materials can have numerous small crystals on the order of 1 to 5 nm dispersed in an amorphous matrix. Magnetic nanocomposite can be materials that have at least one identifiable amorphous region and at least one identifiable crystalline region, thereby making them a composite of amorphous and crystalline structures.

"Aspect Ratio" refers to the ratio between a particle's longest axis and shortest axis.

"Polydispersity" refers to the weight average molecular weight ($M_w$) divided by the number average molecular weight ($M_n$). The polydispersity of a colloidal suspension can be improved by making the c ratio of $M_w/M_n$ closer to 1. Monodisperse refers to particles with a polydispersity less than 1.3.

"Isotropic" refers to a material which has no preferred direction. As used herein it can refer to particles that have a spherical or nearly spherical physical shape, and an amorphous atomic structure. Amorphous structures can be isotropic because the distribution of atoms can be random and uniform in every direction. Crystalline structures can be anisotropic because the crystalline lattice is not uniform in every direction. Spheres can be isotropic and shapes other than a sphere can be anisotropic.

Quantitative detection of proteins in blood and other bodily fluids can be used in the diagnosis of health issues, as it can identify diseases like cancer and bacterial infections before symptoms present. Properties of detection techniques include sufficient sensitivity, multiplexing capacity, and ease of use. Detection techniques include ELISAs, protein microarrays, and quantum dot detection platforms. In these detection techniques, a fluorescent or colorimetric signal can be complicated by autofluorescence or optical absorption from the biological matrix. Similarly, detection techniques including nanowires, microcantilevers, carbon nanotubes, and electrochemical sensors can rely on charge transfer between the sensor and the protein, or tag, of interest. Accurate measurement with these devices can require precise control of sample pH and ionic strength, which can be an unrealistic requirement in practical clinical medicine.

Magnetic assays can be a promising new method because the technology is based on mature electronics technologies and the measurement is simple to perform. Biological samples lack any magnetic background, which can eliminate the need to perform a background calibration or modify the sample before the assay is performed.

Magnetic assays can be limited by the soft magnetic nanoparticles used in their operation, therefore integrating nanoparticle tags with better high frequency susceptibility and magnetic moment can improve the detection limits and sensitivity of this assay.

Other applications for soft magnetic nanoparticles include cored inductors on integrated circuits for high frequency electronic circuits, like those used in cell phones for example, and MEMS on-board power converters. The primary goal in a power conversion circuit can be to change or control the voltage or current levels while minimizing power loss. Two common options are switched-capacitor converters and inductors. Switched-capacitor converters have become the dominant passive component because they are easier scale to smaller sizes but they suffer from fundamental limitations in power conversion efficiency. One of the problems with inductors has been the absence of magnetic core materials which can operate at frequencies above 1 MHz. Air-core inductors, which do not rely on magnetic core materials can be too large for modern integrated circuits. While some amorphous metals used in magnetic sensors can operate at frequencies above 1 MHz, it can be difficult to cheaply and easily integrate these materials into microscale and nanoscale integrated circuits.

One aspect of the disclosed invention is a colloidal suspension of spherical or nearly spherical and amorphous $Co_{91}Zr_9$, $Co_{80}Ti_{20}$, or $Co_{86}Sc_{14}$ particles. The particles can be amorphous and spherical or nearly spherical to reduce anisotropy energy. An amorphous atomic structure eliminates magnetocrystalline anisotropy and a sphere has no shape anisotropy. If the anisotropy energy of a single particle is reduced below 1 to 2 kT and the magnetization remains collinear, then the equilibrium magnetization can be described by the Langevin function:

$$M_z(H,T) = M_{sat} L(\mu H_z/kT) \tag{1}$$

where $M_z$ is the magnetization projection onto the field direction (along the z-axis), $M_{sat}$ is the saturation magnetization, $L = \coth(x) - 1/x$ is the Langevin function, $\mu$ is the particle magnetic moment, and H is the applied field. Since $\mu$ is related to the particle size and saturation magnetization, increasing the particle size or saturation magnetization also increases the magnetic permeability. However, when the demagnetizing field energy of a homogeneously magnetized particle becomes larger than the exchange stiffness energy of the bended magnetization configuration, the magnetization state becomes a vortex or a multi-domain, as demonstrated in FIG. 7. Therefore, in an amorphous particle, the size of μ can be limited by the exchange stiffness constant.

In summary, the material used to form the particles can to be chosen such that: it has a large saturation magnetization, it has a large exchange stiffness, it will form a long lived amorphous state when rapidly cooled, and it is malleable enough to form nearly spherical particles. The material $Co_{91}Zr_9$ exemplifies these properties with $Co_{80}Ti_{20}$ and $Co_{86}Sc_{14}$ being good related materials. Small variations in composition produce similar properties, and so the material may more generally be written as $Co_{1-a}Zr_a$ where larger percentages of Co yield better magnetic properties. Pure Co does not tend to remain amorphous, necessitating some concentration of Zr, so a may be in the range of 0.02 to 0.4. FIG. 1 is a diagram comparing magnetization on the vertical axis vs. magnetic field strength for isotropic ($Co_{92}Zr_8$) based on simulation data.

The magnetization of larger particles can become a vortex or multiple domain. The critical size for this to occur can be estimated by micromagnetic simulations. For $Co_{93}Zr_9$ this critical size can be between 30 and 36 nm as determined from simulations. When the magnetization/saturation magnetization drops below 1, the magnetization is no longer collinear. The desired particle size therefore can be the largest size before value of magnetization/saturation magnetization drops below 1. The desired size range from simulations can therefore be in the range of 25 nm to 38 nm. The average size of the particles that comprise the colloidal suspension may more generally be from 15 to 45 nm, as smaller sized particles can have a collinear magnetization and larger sized particles can still have a collinear magnetization due to small variations in physical properties.

More generally, the composition may be written as $X_{1-a}Y_a$; where X is one of the two elements Co, Fe, Ni or a combination thereof, Y is a transition metal which forms a eutectic with the elements of X, such as Zr, Ti, Sc, Ta, Hf, Y, La, Nd, or a combination thereof and where a is in the range of 0.02 to 0.4. Like Zr, these other elements form a eutectic with Co or Fe and may also create long lived metastable amorphous metal particles when rapidly cooled. The aspect ratio of an ideally spherical particle is 1:1 and it's desirable to have particles which are as close to prefect spheres as possible, although it's difficult to have a colloidal suspension where the particles are all ideal spheres. Therefore, the average aspect ratio of the particles is less than 2:1 or more particularly less than 1.3:1.

Colloidal suspensions of amorphous and spherical or nearly spherical $Co_{91}Zr_9$ can improve on existing technology because common commercial $Fe_3O_4$ particles exhibit decreasing magnetic permeability above 20 nm, which can be due to the increasing magnetocrystalline anisotropy energy. For applications which require both a high magnetic moment per particle and high magnetic permeability, amorphous $Co_{91}Zr_9$ particles exhibit both an increasing magnetic moment per particle and increasing magnetic permeability up to 30 nm or greater.

These magnetic particles can also have the surface of the particles or the solvent is which the particles are suspended modified for various applications. The particles can be coated with Au, $SiO_2$ or carbon, and organic molecules can be attached to the Au, $SiO_2$ or carbon. These particles can be used in biomedical devices such as magnetic immunoassay sensors. The particles can also be dispersed in a polymer for use as a magnetic paste in integrated circuits, for example.

Examples of proteins that can be attached directly to the surface of the particle or to an Au, $SiO_2$ or carbon layer that coats the particle include the following; Anti-CEA and Anti-TIMP1 for the detection of cancer, Anti-PfHRP2 and Anti-PGluDH for the detection of malaria, Anti-cTnI and Anti-hFABP for the detection of cardiac problems, and Anti-ALK and Anti-KRAS for the detection of lung cancer.

Figure 4:
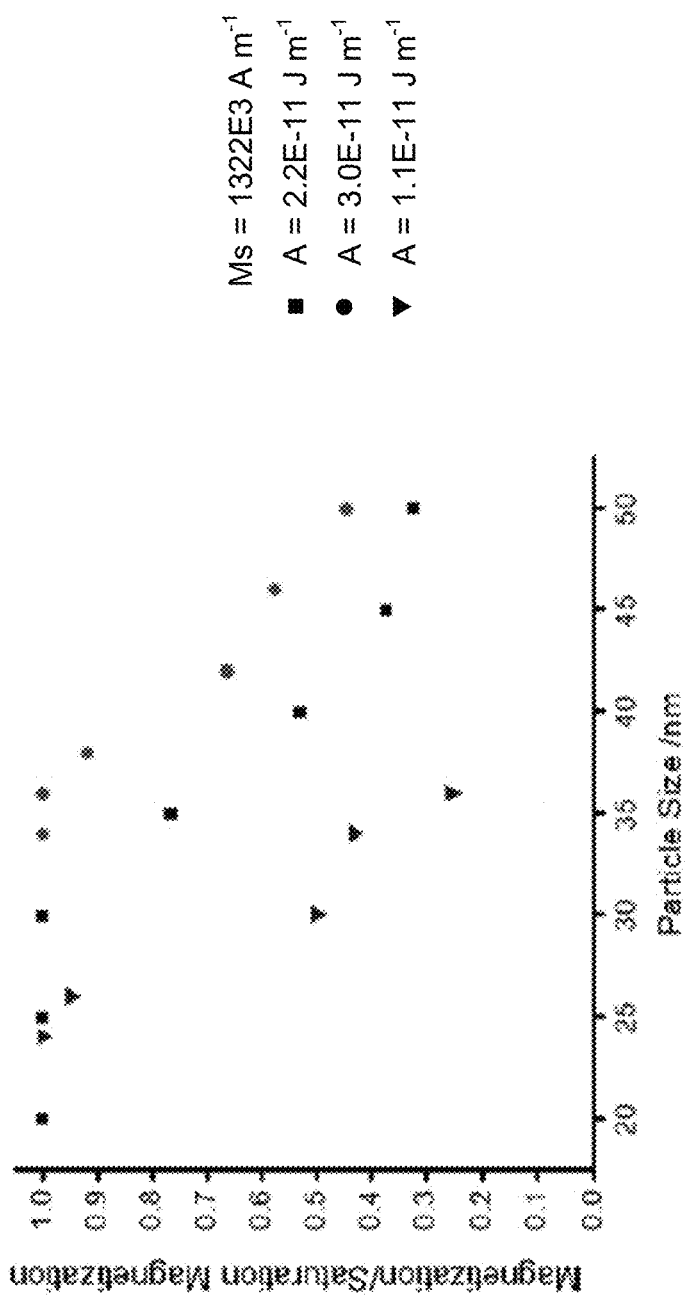
FIG. 4 is a diagram of critical size vs. saturation magnetization in accordance with one disclosed implementation.

Aspects of disclosed implementations provide for the production of a colloidal suspension of isotropic magnetic particles by pulsed laser ablation in liquid. FIG. 4 is a flowchart diagram of a process 400 for manufacturing a colloidal suspension of isotropic magnetic particles. Implementations of this disclosure may change the order of execution of steps of FIG. 4 without departing from the meaning and intent of this disclosure.

At step 401, a desired particle size can be determined using a micromagnetic simulation package, such as the object oriented micromagnetic framework (OOMMF). Knowledge of the target material's saturation magnetization and exchange stiffness can be required. A simulation package is used to determine the size where a bended magnetization configuration becomes the lowest energy state, thereby setting an upper bound for the desired particle size during the production process. Alternatively, the desired size can be determined empirically by examining the magnetic properties of various sized colloids or simply determined based on previous results.

Figure 5:
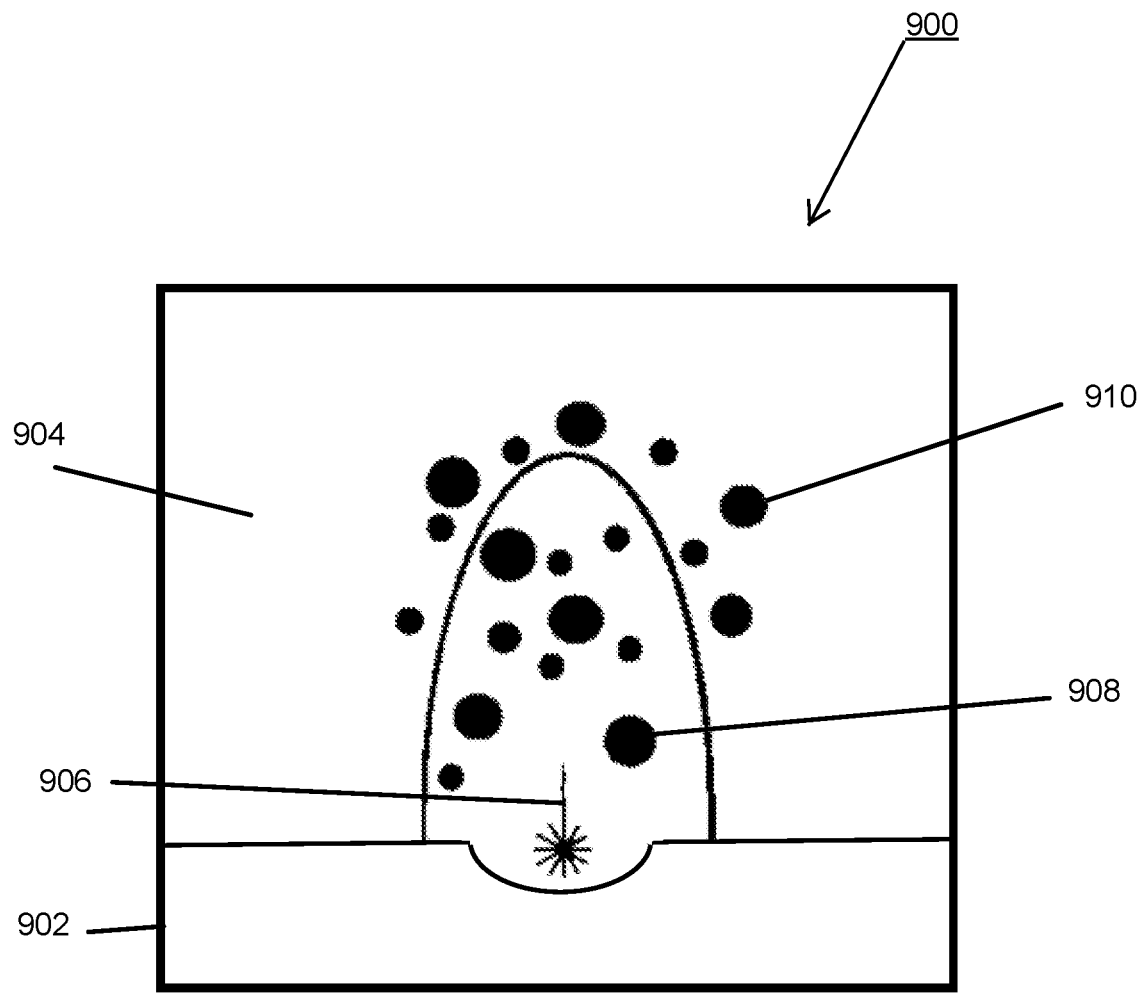
FIG. 5 is a diagram of laser ablation of a target in a solution in accordance with one disclosed implementation.

At step 402 a target with the composition $X_{1-a}Y_a$, where X is one of the group of elements Co, Fe, Ni or a combination thereof, Y is an element from the group of Zr, Ti, Sc, Ta, Hf, Y, La, Nd, or a mixture thereof and a has a value between 0.4 and 0.02 is placed in an organic solvent, for example acetonitrile. The target can have a crystalline or amorphous atomic structure, as steps 402 or 404 can create particles with an amorphous atomic structure. An example of a laser that can be used to irradiate the target is a Ytterbium fiber laser that produces pulses 1 ps to 1 μs in duration at a pulse repetition rate of 10 Hz-200 kHz. The laser can produce an average power of 20 watts and can be focused using laser beam optics to provide pulses having a fluence of at least 10 $J/cm^2$ at the surface of the target. Irradiating the surface of the target creates a colloidal suspension of magnetic nanoparticles in the organic solvent. The beam can be scanned across the surface of the metal so the target face is evenly ablated. FIG. 5 shows a colloidal suspension 900 that includes a target 902 in a solvent 904 being impinged by a laser pulse 906 to create molten particles 908 that quickly cool to form amorphous particles 910.

At this point the colloidal suspension of isotropic magnetic particles can be suboptimal in the sense that the distribution of particles may be broad and particles larger than the desired size can be mixed with particles of the desired size, the colloidal suspension of amorphous magnetic particles can be useful for some applications. At set 402A if it is determined that further processing is desired, the process 400 can proceed to step 404. If no further processing is desired, the process can proceed to step 408.

At step 404, the particle size distribution can be improved by photothermally fragmenting the particles which are too large. To photothermally fragment a particle, the energy absorbed by the particle needs to be larger than the energy necessary to evaporate metal from the surface of the particle. The energy necessary to evaporate metal from the surface of the particle can be calculated from the particle size, the material's boiling point, specific heat capacity, heat of fusion, boiling point, and melting point. The energy that a laser pulse imparts to a particle can be calculated from the absorption cross section of particle, the laser intensity, and pulse duration, for example. The absorption cross section of the particle can be calculated from Mie theory and depends on the particle size. The laser beam diameter in solution can be adjusted to create the desired intensity and thereby fragment particles larger than the desired size. This intensity can be a lower bound, since the particles can also cool during this time and thereby require a greater intensity to fragment.

This photothermal fragmentation process can be allowed to occur for a predetermined time in order to remove particles larger than the desired size and also potentially make particles smaller than the desired size more spherical, as smaller particles may melt and change shape. Step 404 may use the same or a different laser then the one used in step 402. For example, the ablation step may require 5 to 15 minutes, but after the colloid reaches a certain density, the intensity can be attenuated at the target surface by the metal particles created by the laser pulses in solution so ablation is slowed or does not continue. The laser intensity can be attenuated by metal particles absorbing laser energy and thereby beginning to photothermally fragment as described in step 404 while the particle production rate decreases. In this way, during a 1 hour ablation, the first 15 minutes can correspond to step 402 but the remaining 45 minutes can correspond to step 404. In other aspects of disclosed implementations the irradiation at step 402 can be performed using a different laser than the photothermal treatment step at step 404. For example, step 402 can use a pulsed fiber laser and step 404 can use a continuous wave $CO_2$ laser.

An example of step 404 is as follows: the total energy needed to begin evaporation of a 30 nm cobalt particle is determined to be approximately 1.9E-12 J and these particles are known to have an absorption cross section of approximately 50 $nm^2$ at a wavelength of 1060 nm. A 1 ns pulse with a pulse energy of 1 mJ at a wavelength of 1060 nm and a beam diameter of 1 mm provides approximately 3.18E-12 J of energy to the particle, thereby reducing its size though evaporation of metal. This process can also make the particles more spherical, since particles below 30 nm can be melted and amorphous particles favor cooling as spheres. For example, the total energy needed to melt a 22 nm cobalt particle is approximately 3.57E-13 J and the same laser producing pulses with a 1 ns duration and with a pulse energy of 1 mJ and a beam diameter of 1 mm can provide approximately 5E-13 J of energy to the 22 nm particle. Since the 22 nm particle has an absorption cross section of approximately 20 $nm^2$, the laser pulses can at least partially melt the particle and potentially make it more spherical.

At step 404A the process can decide whether or not the size distribution is adequate for the intended application similarly to step 402A. If it is decided that the particles size distribution is adequate for the intended application, the process 400 passes to step 408. If it is decided that further conditioning of the size distribution of particles is required, at step 406 the colloidal suspension of isotropic magnetic particles can be optionally conditioned to remove particles larger than the target size by using a centrifuge or other means to remove particles larger than a desired size. The centrifuge speed necessary to remove particles larger than the desired size determined in step 406 can be calculated or determined empirically.

At step 408 the surface chemistry or solvent can be modified to fit the application. For example, to be used as tags for detecting cancer in magnetic immunoassays, the particles can be dispersed as a stable colloidal suspension in water and proteins can be bound to the particle surface. At step 408 the particles surface can be coated with an inert layer such as Au, $SiO_2$ or carbon. At step 410 the particles can be transferred to water from the solvent. At step 412 proteins can be conjugated to the Au, $SiO_2$ or carbon surface of the particles.

Examples of proteins that may be attached directly to the surface of the particle or to the Au, $SiO_2$ or carbon layer which coats the particle include the following; Anti-CEA and Anti-TIMP1 for the detection of cancer, Anti-PfHRP2 and Anti-PGluDH for the detection of malaria, Anti-cTnI and Anti-hFABP for the detection of cardiac problems, and Anti-ALK and Anti-KRAS for the detection of lung cancer.

Alternatively, the acetonitrile solvent can be replaced with a polymer or a mixture of a polymer and solvent which can dry as a hard paste. This paste can be incorporated into inductors on integrated circuits, or more generally used as a magnetic paste, for example.

Another aspect of disclosed implementations includes spherical or nearly spherical magnetic nanocomposite particles; wherein the particle composition may be written as $X_{1-a-b}Y_aZ_b$ where X is Fe, Co, Ni or a combination thereof, Y includes the transition metals Zr, Ti, Sc, Ta, Hf, Y, La, or Nb and can also include the glass formers B or Si, or a combination thereof, Z is one or more noble metals Cu, Ag, Au or a combination thereof, a is in the range of 0.4 to 0.02, and b is in the range of 0.05 to 0.001. The atomic structure of the particles can be a mixture of amorphous and crystalline regions distributed though the particle's volume, making them a composite of crystalline and amorphous regions. The metal crystals may be Fe, Co, or FeCo depending on the identity of the elements which compose X. One example is the composition $Co_{44}Fe_{44}Zr_6B_5Cu_1$. In this example, the amorphous matrix is composed of CoFeZrBCu and the metal crystals are composed of α-FeCo (BCC) and α'-FeCo (B2). The particles can be spherical or nearly spherical to reduce shape anisotropy, having an aspect ratio less than 2:1 or more particularly having an aspect ratio less than 1.3:1. The exchange stiffness is estimated to be between 1.1 $J\,m^{-1}$ and 2.2 $J\,m^{-1}$, making the desired average size between 10 to 40 nm or more particularly 24 and 30 nm. The variation is size ranges can be because the magnetization of particles smaller than 24 nm can be collinear and particles slightly larger than 30 nm can still be collinear due to small variations in materials.

Compared to the $Co_{91}Zr_9$ particles discussed previously, the exchange stiffness of the magnetic nanocomposite particles with the composition $Co_{44}Fe_{44}Zr_6B_5Cu_1$ can be lower, but the crystallization temperature can be higher, therefore the magnetophoretic mobility can be higher because the saturation magnetization is higher. These particles can be useful for lab-on-a-chip devices which use magnetic fields to both detect and manipulate particles, for example. In this case, they can have organic molecules, such as proteins, bound to their surface, or the particle can be coated with a biologically inert material such as Au, $SiO_2$ or carbon and then the organic molecules can be attached to this biologically inert surface. The large saturation magnetization also makes them useful in integrated circuits and for this application the particles can be dispersed in a mixture of a solvent and polymer, for example.

Figure 6:
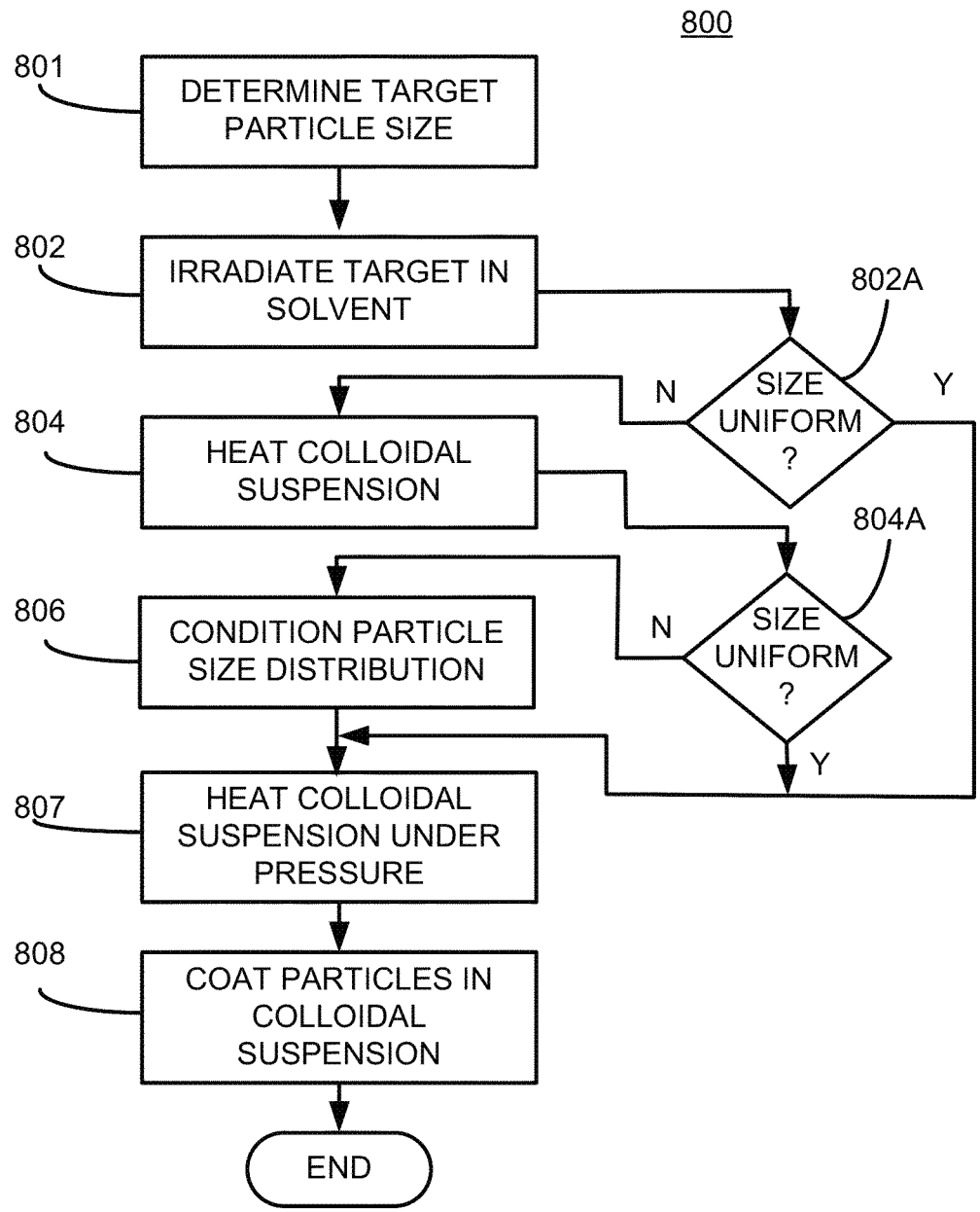
FIG. 6 is a flowchart diagram of a process for manufacturing a colloidal suspension of isotropic magnetic particles in accordance with one disclosed implementation.

Another aspect of disclosed implementations is a technique for producing a colloidal suspension of magnetic nanocomposite particles by pulsed laser ablation in liquid and subsequent thermal treatment. FIG. 6 shows magnetic nanocomposite particles produced by adapting process 400 to form process 800 by specifying additional thermal treatment. At step 801 the target particle size can be determined as described above. At step 802, a target of the form $X_{1-a-b}Y_aZ_b$, where X is Co, Fe, or a combination thereof, Y includes the transition metals Zr, Ti, Sc, Ta, Hf, Y, La, and Nb, and can also include the glass formers B or Si, or a combination thereof, Z is one or more noble metals Cu, Ag, Au, or a combination thereof, a is in the range of 0.4 to 0.02, and b is in the range of 0.05 to 0.001 is irradiated by laser pulses as shown in FIG. 9; An example of one such target can be $Co_{44}Fe_{44}Zr_6B_5Cu_1$. As was describe above, the atomic structure of the target may be crystalline or amorphous. If it is determined at step 802A that the particles require further processing to make the particle size more consistent, at step 804 the particles in solvent are heated as described above.

Other aspects of disclosed implementations include systems, methods, and apparatuses for manufacturing a colloidal suspension of nanocomposite particles including irradiating, with a pulsed laser, a target in a solvent wherein the pulsed laser produces laser pulses having a pulse duration between 1 ps and 1 μs at a wavelength between 200 nm and 1500 nm and a fluence of at least 2 J/cm² with a repetition rate greater than 10 Hz. The beam can be scanned across the surface of the target and the target can include a metallic composite with the composition $X_{1-a-b}Y_aZ_b$, where X can be the magnetic elements Co, Fe or Ni or a mixture thereof, Y is a transition metal or glass former which forms a eutectic with the elements of X, such as the transition metals Zr, Ti, Sc, Ta, Hf, Y, La, Nd or the glass formers Si or B or a combination thereof; where Z is one of the group of elements Au, Ag and Cu; where a has a value between 0.4 and 0.02 and b has a value between 0.05 and 0.001. The solvent can be an organic solvent and photothermal fragmentation can be used to modify the size or shape of the particles which comprise the colloidal suspension. Centrifugation can be used to further modify the size of the particles included in the colloidal suspension. After the desired size distribution is obtained, the particles can be sealed in a high pressure vial and heated to between 100 and 800° C. for at least 2 min to induce nucleation of metal crystallites in the particle. The surface of the particles or the composition of the solvent can be changed to suit the application, which can include modifying the surface of the particles with Au, $SiO_2$, C or a polymer, or can include replacing part or the entirety of the solvent with a polymer or another solvent. The method can further include attaching organic molecules including proteins to the surface of the particles or to the surface of the Au, $SiO_2$, C or polymer which coats the particles.

Figure 3:
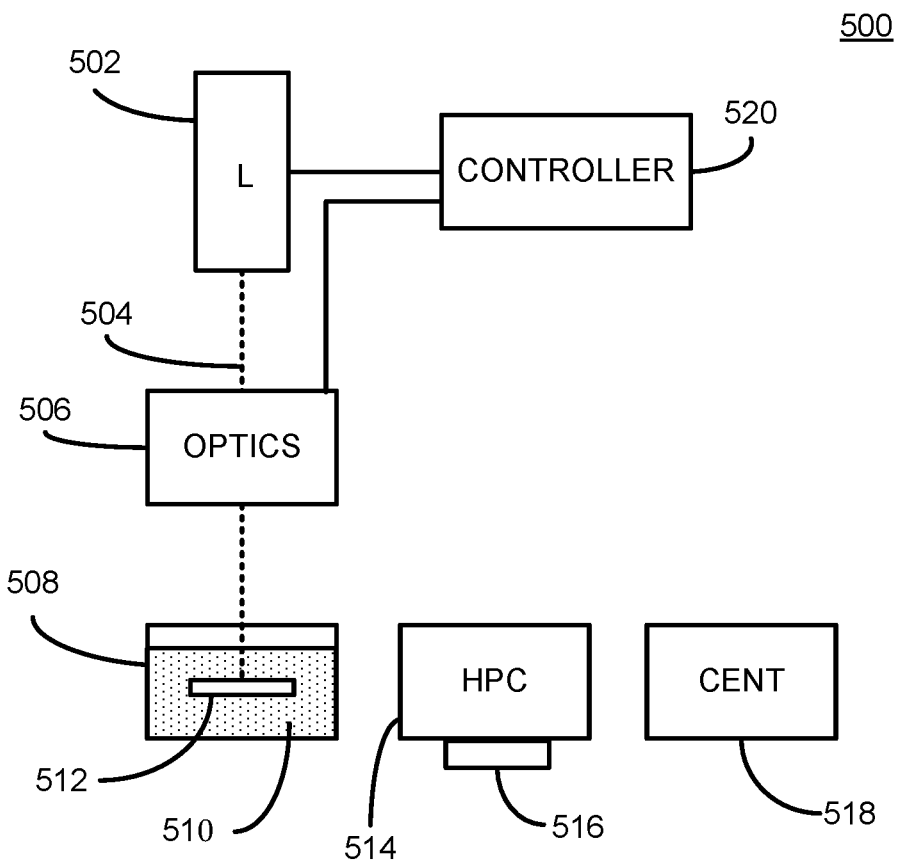
FIG. 3 is a diagram of a system for manufacturing a colloidal suspension of magnetic nanocomposite particles in accordance with one disclosed implementation.

FIG. 3 is a diagram of a system 500 for manufacturing magnetic nanocomposite particles according disclosed implementations. System 500 includes a laser 502 that emits a pulsed laser beam 504 under the control of a controller 520. The laser 502 can be an Ytterbium fiber laser, for example. The controller 520 can be a computing device having a CPU and memory, the CPU operative to execute instructions stored in the memory to direct the system 500 perform the activities related to manufacturing nanocomposite materials disclosed herein. The pulsed laser beam 504 can be directed to a specimen 512 by laser optics 506. Laser optics 506 can include beam and pulse shaping optics that shape the laser beam pulses temporally and spatially to direct the pulsed laser beam 504 to a focal point at or near the surface of the specimen 512. The laser optics 506 may also include a scanner. The specimen 512 can be included in a specimen container 508 that holds an organic solvent 510 within which the specimen 512 is submerged. The pulsed laser beam 504 creates a colloidal suspension of magnetic nanoparticles in the organic solvent 510 by impacting the surface of the specimen 512.

System 500 also includes a high pressure container 514 and a heat source 516 for heating the colloidal suspension nanoparticles resulting from applying the pulsed laser beam 504 to the specimen 512 in the organic solvent 510. Also included in system 500 is a centrifuge 518 which can be used to further condition the size distribution of the magnetic nanoparticles in colloidal suspension in the organic solvent 510.

FIG. 4 is a graph of critical sizes for three particles with a saturation magnetization of 1422E3 A m⁻¹ and exchange stiffness constants of 2.2E-11, 3.0E-11, and 1.1E-11 respectively. As can be seen from FIG. 4, as particle size increases saturation magnetization decreases, with the onset and rate of decrease dependent upon exchange stiffness constants for each particle. Critical size can be determined for each particle by the largest size achievable before saturation magnetization begins to decline. The critical sizes, J m⁻¹, for these three particles are 30 nm, 36 nm, and 25 nm, respectively.

Figure 7:
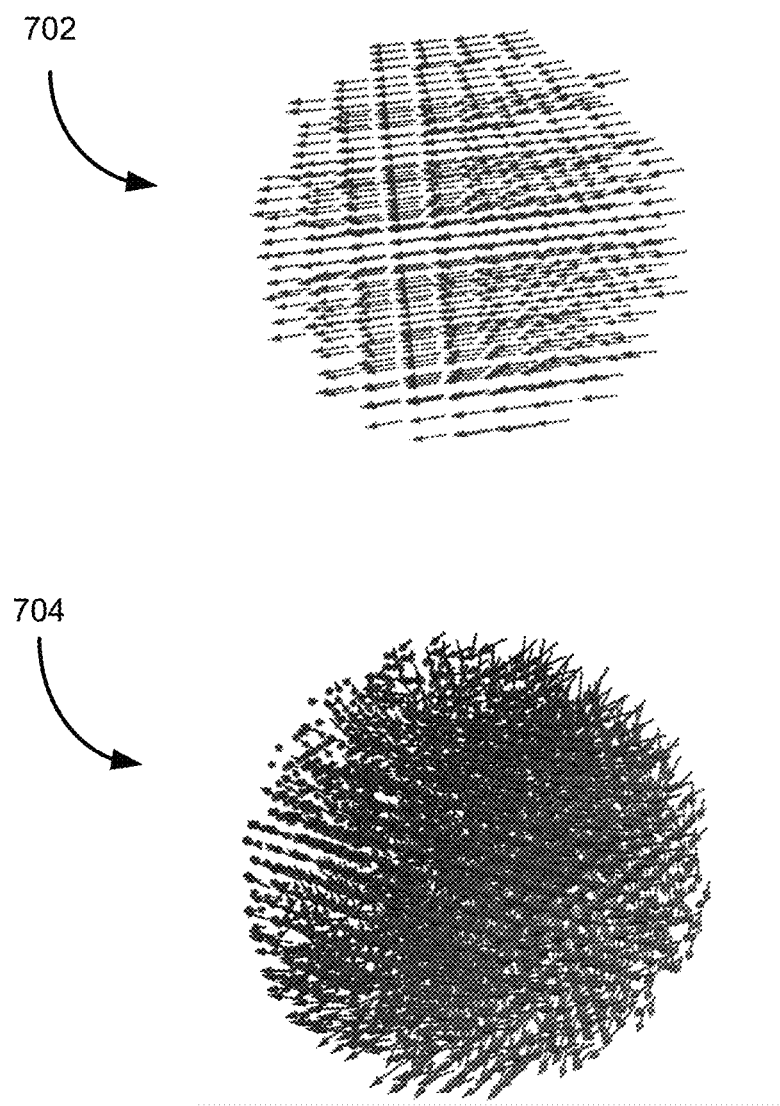
FIG. 7 is a diagram of magnetic particles with vortex and collinear magnetization.

FIG. 7 is a diagram of two particles, one with a collinear magnetization 702 and one with a vortex magnetization 704. Particles with collinear magnetization can correspond to particles under the critical size as determined by the graph in FIG. 6, for example. Particles with a vortex magnetization are too large as determined by the graph in FIG. 6 and can be removed from the solution using techniques described above The words "example" or "exemplary" are used herein to mean serving as an example, instance, or illustration. Any aspect or design described herein as "example' or "exemplary" is not necessarily to be construed as preferred or advantageous over other aspects or designs. Rather, use of the words "example" or "exemplary" is intended to present concepts in a concrete fashion. As used in this application, the term "or" is intended to mean an inclusive "or" rather than an exclusive "or". That is, unless specified otherwise, or clear from context, "X includes A or B" is intended to mean any of the natural inclusive permutations. That is, if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from context to be directed to a singular form. Moreover, use of the term "an embodiment" or "one embodiment" or "an implementation" or "one implementation" throughout is not intended to mean the same embodiment or implementation unless described as such.

A computing device implementing the techniques disclosed herein (and the algorithms, methods, instructions, etc. stored thereon and/or executed thereby) can be realized in hardware, software, or any combination thereof including, for example, IP cores, ASICS, programmable logic arrays, optical processors, molecular processors, quantum processors, programmable logic controllers, microcode, firmware, microcontrollers, servers, microprocessors, digital signal processors or any other suitable circuit or other information processing device, now existing or hereafter developed. In the claims, the term "processor" should be understood as encompassing any the foregoing hardware, either singly or in combination. The terms "signal" and "data" are used interchangeably.

Further, in one embodiment, for example, the techniques described herein can be implemented using a general purpose computer or general purpose processor with a computer program that, when executed, carries out any of the respective methods, algorithms and/or instructions described herein. In addition or alternatively, for example, a special purpose computer/processor can be utilized which can contain specialized hardware for carrying out any of the methods, algorithms, or instructions described herein.

Further, all or a portion of embodiments of the present disclosure can take the form of a computer program product accessible from, for example, a tangible computer-usable or computer-readable medium. A computer-usable or computer-readable medium can be any device that can, for example, tangibly contain, store, communicate, or transport the program for use by or in connection with any processor. The medium can be, for example, an electronic, magnetic, optical, electromagnetic, or a semiconductor device. Other suitable mediums are also available.

What is claimed is:

1. Magnetic particles comprising:
   isotropic particles having the general formula $X_{1-a}Y_a$, where X is one of Co, Fe or a combination of Co and Fe,
   Y is at least one of Zr, Ti, Sc, Ta, Hf, Y, La, Si, B, Nd, either individually or in combination,
   a has a value between 0.4 and 0.02, and
   the isotropic particles have an average particle size between 15 and 45 nm, an aspect ratio of less than 5:1, and an amorphous atomic structure.

2. The magnetic particles of claim 1 wherein the isotropic particles further include a component Z and have the structure $X_{1-a}Y_aZ_b$, wherein Y is one or more of the following: Zr, Ti, Sc, Ta, Hf, Y, Nd, Si, B,
   Z is at least one of the Group 11 elements Au, Ag, Cu, and
   b has a value between 0.05 and 0.001.

3. A colloidal suspension comprising:
   a solvent; and
   the magnetic particles of claim 1.

4. The composition of claim 3, wherein the isotropic particles are coated with an inert material including at least one of $SiO_2$, Au, C.

5. The composition of claim 4, wherein the isotropic particles further comprise:
   a biocomponent, the biocomponent being one or more of protein or nucleic acid, the biocomponent attached to the inert material to create a targeted magnetic particle.

6. The composition of claim 5, wherein the protein is bound to a surface of an isotropic particle and is Anti-CEA or Anti-TIMP1.

7. A particulate material comprising:
   nanocomposite magnetic particles having the general formula $X_{1-a-b}Y_aZ_b$, where X is Co, Fe, Ni, or a combination of one or more of Co, Fe, or Ni,
   Y is one of Zr, Ti, Sc, Ta, Hf, Y, La, Nd, Si, B, or a combination of one or more of Zr, Ti, Sc, Ta, Hf, Y, La, Nd, Si, or B,
   Z is one of Au, Ag, Cu, or a combination of one or more of Au, Ag or Cu,
   a has a value between 0.4 and 0.02,
   b has a value between 0.05 and 0.001,
   the nanocomposite magnetic particles have an average particle size between 15 and 45 nm and an aspect ratio of less than 5:1, and
   the atomic structure of the composition is one of an amorphous structure, a structure of crystallites between 1 and 5 nm, or a combination of the amorphous structure and the structure of crystallites between 1 and 5 nm.

8. A colloidal suspension comprising:
   a solvent; and
   the magnetic particles of claim 7.

9. The composition of claim 8, wherein the nanocomposite magnetic particles are coated with an inert material including at least one of $SiO_2$, Au, C.

10. The composition of claim 9, wherein the nanocomposite magnetic particles further comprise a protein or nucleic acid attached to the inert material to create a targeted magnetic particle.

11. The composition of claim 10, wherein the protein is Anti-CEA or Anti-TIMP1.

* * * * *